(12) United States Patent
Martinelli et al.

(10) Patent No.: US 6,500,177 B1
(45) Date of Patent: Dec. 31, 2002

(54) TELESCOPIC BODY FOR AN EXTERNAL FIXATION SYSTEM

(75) Inventors: Orlando Martinelli, Bern (CH); Beat Inauen, Hölstein (CH); Erwin Flühler, Allschwil (CH); Lutz Claes, Neu-Ulm (DE); Heinz Gerngross, Ulm (DE); Götz Rübsaamen, Traunstein (DE)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/714,108

(22) Filed: Nov. 17, 2000

Related U.S. Application Data

(63) Continuation of application No. PCT/CH98/00206, filed on May 19, 1998.

(51) Int. Cl.⁷ ............................................... A61B 17/60
(52) U.S. Cl. .......................................... 606/57; 606/54
(58) Field of Search .............................. 606/53, 54, 55, 606/56, 57, 58, 59, 60, 62, 63

(56) References Cited

U.S. PATENT DOCUMENTS

| | | | |
|---|---|---|---|
| 1,997,466 A | 4/1935 | Longfellow |
| 2,198,871 A | 4/1940 | Haboush |
| 2,238,870 A | 4/1941 | Haynes |
| 2,250,417 A | 7/1941 | Ettinger |
| 2,251,209 A | 7/1941 | Stader |
| 2,333,033 A | 10/1943 | Mraz |
| 2,346,346 A | 4/1944 | Anderson |
| 2,391,537 A | 12/1945 | Anderson |
| 2,391,693 A | 12/1945 | Ettinger |
| 2,393,694 A | 1/1946 | Kirschner |
| 2,432,695 A | 12/1947 | Speas |
| 3,727,610 A | 4/1973 | Riniker |
| 4,024,860 A | 5/1977 | Chelnokov et al. |
| 4,308,863 A | 1/1982 | Fischer |
| 4,312,336 A | 1/1982 | Danieletto et al. |
| 4,456,004 A | 6/1984 | Kenny |
| 4,475,546 A | 10/1984 | Patton |
| 4,488,542 A | 12/1984 | Helland |
| 4,502,473 A | 3/1985 | Harris et al. |
| 4,570,625 A | 2/1986 | Harris et al. |

(List continued on next page.)

FOREIGN PATENT DOCUMENTS

| | | |
|---|---|---|
| DE | 3614305 A1 | 11/1987 |
| DE | 9319433 | 3/1994 |
| EP | 0 011 258 | 5/1980 |
| EP | 0 424 292 A2 | 4/1991 |
| EP | 0 858 781 A2 | 8/1998 |
| GB | 2 223 406 A | 4/1990 |
| JP | 8-299361 | 11/1996 |
| JP | 10-043204 | 11/1997 |
| JP | 10-174695 | 5/1998 |
| JP | 10-225465 | 8/1998 |
| JP | 10-225466 | 8/1998 |
| WO | WO 83/02554 | 8/1983 |
| WO | WO 91/11149 | 8/1991 |

*Primary Examiner*—David O. Reip
(74) *Attorney, Agent, or Firm*—Pennie & Edmonds LLP

(57) ABSTRACT

A telescopic body for an external bone fixation device includes a central core body and cylindrical outer parts having a bore extending therethrough, all disposed about a center axis. The outer surface of the core body is in the form of a keyed shaft, and the bore in the outer parts has keyways that mate with the shaft, thereby permitting the outer parts to be telescoped in a rotationally fixed, torsion-resistant fashion. Threaded drive spindles housed in the outer parts can be screwed into and out of the core body at either end, permitting the overall length of the telescopic body to be changed. Terminal elements are provided in the ends of the outer parts to limit travel of the drive spindles. At least one of the terminal elements may be a dynamic progression cap which, when progressively unscrewed, allows the axial clamping tension of the threaded spindle to be released in millimeter increments to permit relaxation of the axial clamping of the spindle. The degree of rigidity of the telescopic body as a whole is selectable by suitable choice of materials for each component.

20 Claims, 3 Drawing Sheets

U.S. PATENT DOCUMENTS

| | | |
|---|---|---|
| 4,576,158 A | 3/1986 | Boland |
| 4,611,586 A | 9/1986 | Agee et al. |
| 4,612,921 A | 9/1986 | Lazo de Zbikowski |
| 4,621,627 A | 11/1986 | DeBatiani et al. |
| 4,628,919 A | 12/1986 | Clyburn |
| 4,628,922 A | 12/1986 | Dewar |
| 4,730,608 A | 3/1988 | Schlein |
| 4,745,913 A | 5/1988 | Castaman et al. |
| 4,848,368 A | 7/1989 | Kronner |
| 4,922,896 A | 5/1990 | Agee et al. .............. 606/55 |
| 4,978,348 A | 12/1990 | Ilizarov ................ 606/57 |
| 4,988,349 A | 1/1991 | Pennig ................. 606/58 |
| 5,080,661 A | 1/1992 | Lavender et al. ........... 606/54 |
| 5,160,335 A | 11/1992 | Wagenknecht |
| 5,207,676 A | 5/1993 | Canadell et al. ............ 606/54 |
| 5,275,599 A | 1/1994 | Zbikowski et al. ........... 606/54 |
| 5,314,426 A | 5/1994 | Pohl et al. .............. 606/58 |
| 5,439,465 A | 8/1995 | Tumibay ................ 606/105 |
| 5,454,810 A | 10/1995 | Pohl et al. .............. 606/59 |
| 5,527,309 A | 6/1996 | Shelton ................ 606/55 |
| 5,591,164 A | 1/1997 | Nazre et al. .............. 606/59 |
| 5,601,551 A | 2/1997 | Taylor et al. ............. 606/54 |
| 5,620,449 A | 4/1997 | Faccioli et al. ............ 606/98 |
| 5,643,258 A | 7/1997 | Robioneck et al. .......... 606/54 |
| 5,653,707 A | 8/1997 | Taylor et al. ............. 606/54 |
| 5,662,648 A | 9/1997 | Faccioli et al. ............ 606/54 |
| 5,674,221 A | 10/1997 | Hein et al. .............. 606/54 |
| 5,688,271 A | 11/1997 | Faccioli et al. ............ 606/54 |
| 5,690,633 A | 11/1997 | Taylor et al. ............. 606/73 |
| 5,738,684 A | 4/1998 | Thomas et al. ............ 606/54 |
| 5,741,252 A | 4/1998 | Mazzio et al. ............ 606/54 |
| 5,766,173 A | 6/1998 | Ross, Jr. et al. ........... 606/56 |
| 5,788,700 A | 8/1998 | Morawa et al. ............ 606/88 |
| 5,863,292 A * | 1/1999 | Tosic ................. 606/56 |
| 5,928,230 A | 7/1999 | Tosic ................. 606/57 |
| 5,951,556 A | 9/1999 | Faccioli et al. ............ 606/65 |
| 6,001,097 A | 12/1999 | Campopoano et al. ........ 606/57 |
| 6,007,534 A | 12/1999 | Gonzalez et al. ........... 606/54 |
| 6,024,745 A | 2/2000 | Faccioli et al. ............ 606/54 |
| 6,030,386 A | 2/2000 | Taylor et al. ............. 606/56 |
| 6,036,691 A | 3/2000 | Richardson .............. 606/57 |
| 6,102,911 A | 8/2000 | Faccioli et al. ............ 606/54 |
| 6,176,860 B1 | 1/2001 | Howard ................ 606/54 |
| 6,203,548 B1 | 3/2001 | Helland ................ 606/105 |

* cited by examiner

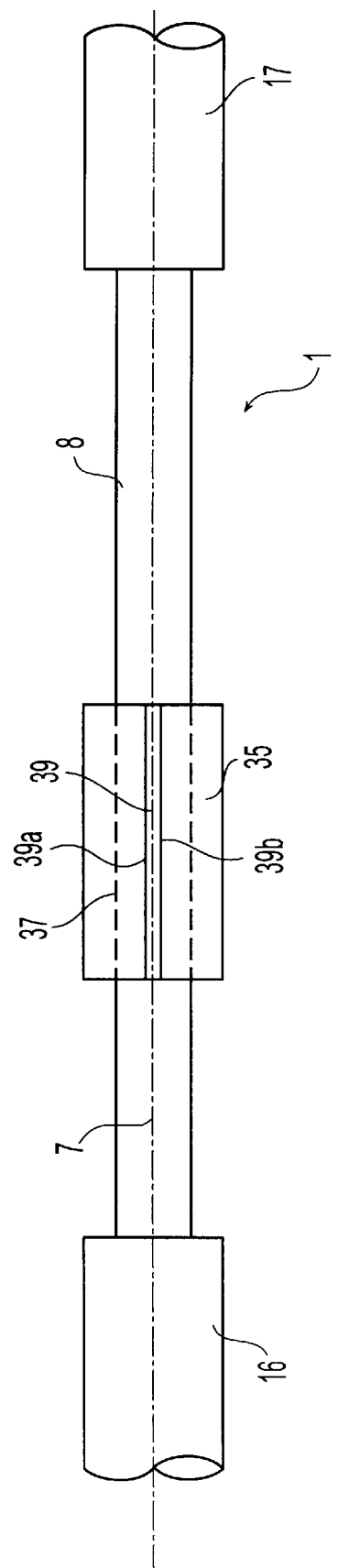

TELESCOPIC BODY FOR AN EXTERNAL FIXATION SYSTEM

CROSS-REFERENCE TO RELATED APPLICATIONS

This application is a continuation of the U.S. National Stage designation of co-pending International Patent Application PCT/CH98/00206, filed May 19, 1998, the entire content of which is expressly incorporated herein by reference thereto.

FIELD OF THE INVENTION

The invention relates to a device for use in the external fixation of parts of broken bones. More particularly, the invention relates to a telescopic body about which components of an external fixation system are mounted.

BACKGROUND OF THE INVENTION

A number of devices for use in the external fixation of bones are already known. One such device is disclosed in EP 0 011 258 A1 to ORTHOFIX, and includes an elongated central body with two parts that can be shifted relative to each other and parallel to the longitudinal axis of the central body. Each of the parts of the central body support a clamping unit for use in the insertion of nails or bone screws in a bone section, and a pressure and traction element acts on the two parts of the central body. The clamping units are ball-joint-mounted at the ends of the movable parts in a manner as to permit three-way rotation of the clamping units as well as the nails or screws intended for insertion in the bone sections.

Another fixation rod for the external fixation of bones is disclosed in U.S. Pat. No. 5,160,335 to Wagenknecht. The fixation rod is telescopable if necessary, and includes connecting parts having curved support surfaces for receiving clamping elements that hold bone-fastening pins. Brackets are used to attach the clamping elements supporting the connecting parts to the fixation rod. The connecting parts permit three-way rotation of the clamping elements relative to the brackets.

Although the fixation rod used with these external fixation devices is telescopable in a sense in that it permits parts mounted thereon to be moved relative to each other, the drawback in the case of both of these earlier devices is that the movement of the parts is brought about by a pressure and traction element that is externally attached to the fixation rod and/or with the aid of a clamping screw on the fixation rod. In addition, the fixation rod of these devices permits extension at one end only, and/or does not have a uniform diameter over its entire length. Thus, fastening clamps cannot be mounted at all possible desired points along the fixation rod.

There exists a need for an improved connecting element which is extensible internally as well as at both ends, thus permitting bilateral extension that advantageously may reduce the duration of the external fixation treatment. Such a reduction in treatment duration may even realize a fifty percent decrease in time. There further exists a need for an improved connecting element with a rigidity that is selectable due to the interchangeability of the various parts that are formed from different materials. The present invention provides an improved connecting element that is capable of providing these improvements.

SUMMARY OF THE INVENTION

The present invention is related to an external bone fixation device. The device includes a first support having outer and inner surfaces, a pair of second supports slidably engagable with the outer surface of the first support, and a driving mechanism disposed at least partially in contact with the inner surface of the first support. The first support, second supports, and driving mechanism are coaxially disposed about a center axis, and engagement of the driving mechanism with the first support permits the device to change overall length without rotation of the first and second supports with respect to each other. The second supports are hollow and have outer and inner surfaces, with the inner surface of each second support being at least partially in contact with the outer surface of the first support. The first support has proximal and distal ends, with the driving mechanism being engagable with at least one of the ends.

In one embodiment, the driving mechanism comprises at least one shaft threadably associated with the inner surface of the first support. The axial locations of the at least one shaft and at least one of the second supports along the center axis are fixed with respect to each other. Typically, the axial locations of the at least one shaft and at least one of the second supports along the center axis are movable with respect to each other.

In another embodiment, the driving mechanism has two shafts threadably associated with the inner surface of the first support, with each shaft being independently engageable with an end of the first support. Each second support has a proximal end and a distal end, and the device further includes at least one cap for bearing against an end of the shaft that is operatively associated with that support at the distal end of each second support. At least one of the caps is movable with respect to its respective second support so that the shaft associated with that support is permitted to move axially along the central axis therewith.

Typically, the second supports have a uniform diameter over substantially their entire length, and the first support is keyed and mates with keyways formed in the inner surfaces of the second supports to prevent rotation therebetween.

In another embodiment, the device includes an intermediate support positioned between the second supports and disposed upon the first support about the central axis. The intermediate support and the second supports have outer diameters that are substantially the same, and the intermediate support has a longitudinal slot to facilitate placement of the intermediate support on the first support.

BRIEF DESCRIPTION OF THE DRAWINGS

Preferred features of the present invention are disclosed in the accompanying drawings, wherein similar reference characters denote similar elements throughout the several views, and wherein:

FIG. 3 is a partial cross-sectional view of another connecting element of the present invention.

DETAILED DESCRIPTION OF PREFERRED EMBODIMENTS

Figure 1:
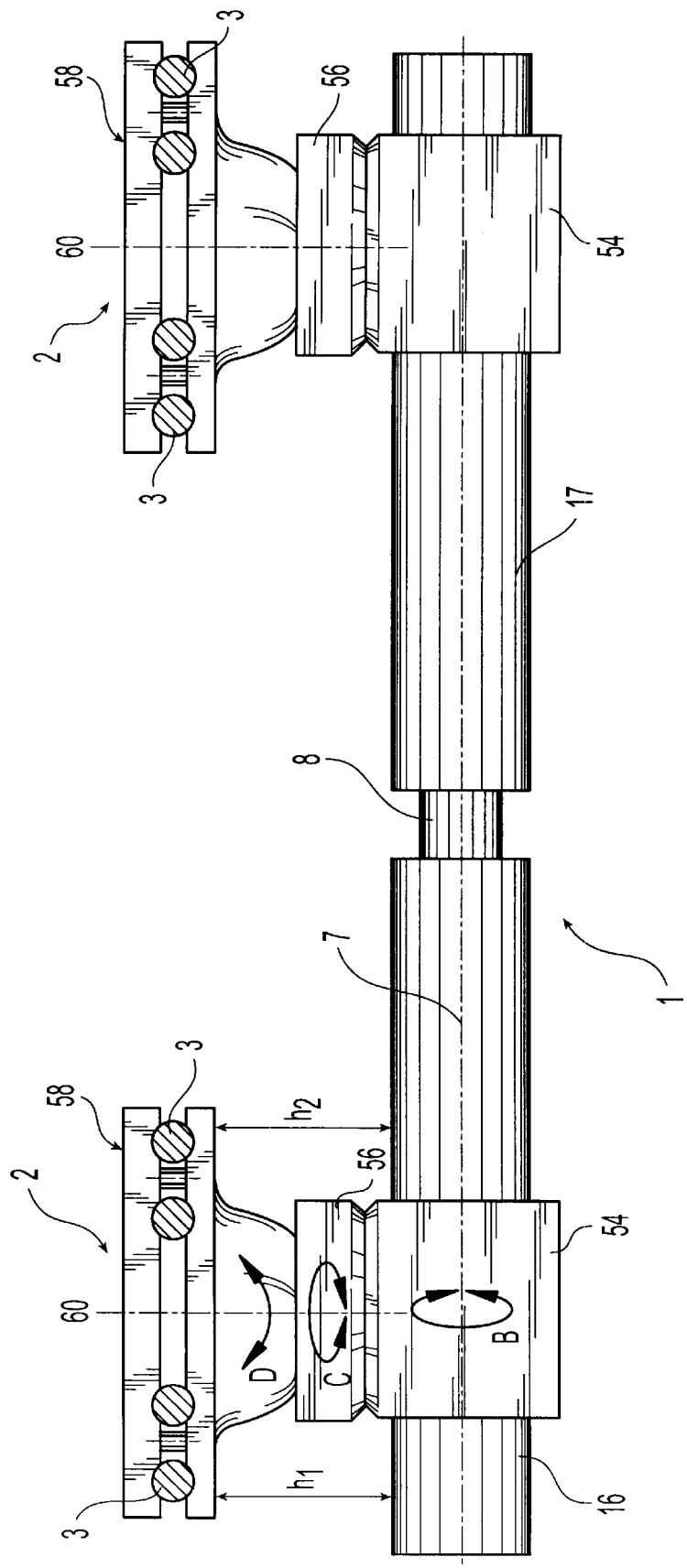
FIG. 1 is an elevational view of a connecting element of the present invention, with two fastening clamps for the fixation of bone screws mounted thereon.

The present invention is related to a device for the external fixation of parts of broken bones. The device includes a longitudinal connecting element having a center axis. The connecting element is bilaterally telescopable along the center axis in a torsionally rigid, rotationally immobile fashion, and permits the detachable mounting of fastening jaws thereto for the fixation of bone screws or pins. The connecting element includes a central part or core body and two outer parts which can be positionally shifted along the center axis on the core body. The movable outer parts permit the connecting element to be bilaterally extensible. The connecting element also may have a uniform diameter over its entire length. The axial position of the outer parts relative to the core body is both adjustable and lockable by means of drive elements provided inside the outer parts. The exchangeability of the core body and of the outer parts allows for a selectable degree of rigidity of the connecting element, with the exchangeable components formed from different materials.

The connecting element may include a generally cylindrical central part or core body and two concentric hollow-cylindrical outer parts. The outer surfaces of the outer parts extend coaxially with the center axis and are rotationally symmetrical. The outer parts can slide axially on the core body and permit torsion-free telescoping. The core body may have an externally polygonal cross section and the outer parts may have an internally polygonal cross section for mating therewith. The polygonal shapes of the components permit the outer parts to slide axially on the central core body, and also permit telescoping of the outer parts without torsional movement relative to each other or to the core body.

The outer surface of the core body may be in the form of a keyed shaft. The outer parts are formed with a cross section having an internal configuration that matches the profile of the keyed shaft.

The present invention further is related to a device that permits the axial position of the outer parts on the core body to be lockable, and also to be adjustable via threaded drive spindles. The threaded drive spindles can be screwed into and out of the core body. The drive spindles may be lockable in their position by means of terminal elements which can be screwed into the outer parts. At least one of the terminal elements may be a dynamic progression cap which, when progressively unscrewed, allows the axial clamping tension of the threaded spindle to be released in millimeter increments so that millimeter-by-millimeter relaxation of the axial clamping of at least one drive element is achieved. An elastic collar may also be provided on the dynamic adjustment end cap. Thus, the outer part may be axially moved by a controllable amount, permitting dynamic adjustment of the fracture.

The present development also is related to a device having at least one intermediate element that can be mounted on the core body between the outer parts. The intermediate element is axially movable on the core body, but rotationally immobile, and can be locked in a given axial position on the core body. Also, the intermediate element has the same outer diameter as the outer parts so that it can be equipped with one or several fastening jaws for the detachable fixation of bone screws or pins. The at least one fastening jaw can be mounted on the circumferential surface of the intermediate element. The intermediate element is longitudinally split by a continuous through-slot on one side along the center axis, and locked in position on the core body by the clamping force of a clamping jaw mounted on the slotted intermediate element. Alternatively, instead of a single slot, the intermediate element may be provided with two continuous slots on two opposite sides along the center axis.

Figures 2, 2A:
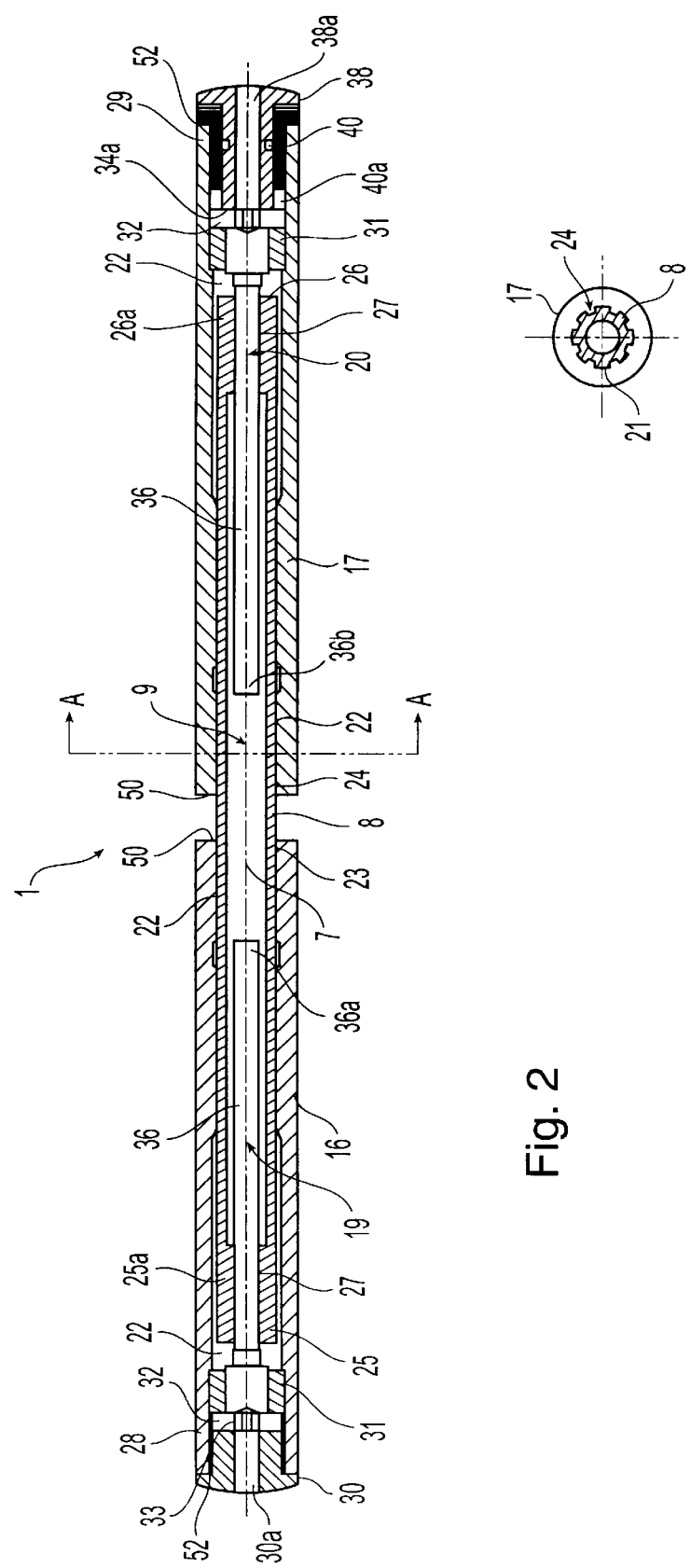
FIG. 2 is a cross-sectional view of the connecting element of FIG. 1.
FIG. 2A is a cross-sectional view of the connecting element of FIG. 2, taken along line A—A.

Referring to FIGS. 1–3, a telescopic tubular body for an external bone fixation device is shown in the form of a connecting element 1. Connecting element 1 includes a central core body 8 and cylindrical outer parts 16, 17, all disposed about a center axis 7. Preferably, outer parts 16, 17 are hollow, each having a bore 22 extending from a proximal end 50 to a distal end 52. With cylindrical outer parts 16, 17 disposed on central core body 8, connecting element 1 may be telescoped in both directions along center axis 7 through the slidable engagement of core body 8 and outer parts 16, 17. Thus, the overall length of the assembled connecting element 1 may be varied.

Fastening jaws 2 for holding and attaching bone screws 3 are detachably mountable on outer parts 16, 17, the jaws 2 being axially positionable along center axis 7. Although connecting element 1 is shown in FIG. 1 supporting two jaws 2, additional jaws 2 can be accommodated. In a preferred embodiment, jaws 2 include a lower portion 54, intermediate portion 56, and upper portion 58. Lower portion 54 is configured for mounting upon outer parts 16, 17, and may exert a clamping force on an outer part 16, 17 so that jaw 2 may be held at a fixed location on the outer part 16, 17. Furthermore, lower portion 54 may be configured and dimensioned to permit rotation on a cylindrical outer part 16, 17 about center axis 7, as generally shown by arrow B.

Portions 54, 56, 58 of each jaw 2 may be generally disposed about an axis 60 running transverse to center axis 7. Intermediate portion 56 may be coupled to lower portion 54, such that intermediate portion 56, and the upper portion 58 carried thereon, may be rotated about axis 56 as shown generally with arrow C. In addition, positioning of bone screws 3 may be adjusted by moving upper portion 58 of jaw 2 about axis 60 in the direction of arrow D, such that vertical distances $h_1$ and $h_2$ between upper portion 58 and an outer part 16, 17 may be changed. The separation distance between a pair of jaws 2 each mounted on an outer part 16, 17 may be changed independently of the mounting of lower portion 54 on each outer part 16, 17, due to the ability of connecting element 1 to telescope along center axis 7.

In the preferred embodiment, in order to facilitate telescopic, axial movement, each outer part 16, 17 and core body 8 are hollow. Preferably, as shown for example in FIG. 2A, the outer surface 21 of core body 8 is in the form of a keyed shaft that is rotationally symmetric. The inner portions 23, 24 of bores 22 of outer parts 16, 17 are configured and dimensioned to mate with keyed outer surface 21, thereby permitting outer parts 16, 17 to be telescoped in a rotationally fixed, torsion-resistant fashion. The same configuration is obtained by taking a cross-section through outer part 16 near proximal end 50.

In alternate embodiments, the outer surface of core body 8 and the inner portions of outer parts 16, 17 have other matching configurations such as cylindrical portions or other polygonal shapes.

Core body 8 includes a bore 9 disposed about center axis 7 that extends from a first end 25 to a second end 26. Preferably, ends 25, 26 include internal, threaded shoulder portions 25a, 26a, respectively. A pair of opposing, threaded spindles 19, 20 are disposed about center axis 7 and extend into bore 9 of core body 8. Spindles 19, 20 have rims 32 as well as shaft portions 36 which threadably engage shoulder portions 25a, 26a, respectively.

Sleeves 31 are disposed inside each bore 22 in outer parts 16, 17 proximate end portions 28, 29, respectively, the sleeves being fixed therein. End caps 30, 38 are disposed in distal ends 52 of bores 22 of outer parts 16, 17, respectively, such that rims 32 of spindles 19, 20 are disposed between end caps 30, 38 and sleeves 31, and thus are fixed in axial position within outer parts 16, 17.

Axial movement of outer parts 16, 17 is thus facilitated by the interaction of core body 8 and spindles 19, 20. With threaded spindles 19, 20 positionally fixed within outer parts 16, 17, screw action of lead-screw-type shaft portions 36 within threaded shoulder portions 25a, 26a permits spindles 19, 20 to rotate about center axis 7, and thus the separation distance between spindle ends 36a, 36b and ends 25, 26 of core body 8, respectively, may be adjusted. Likewise, the overall axial length of connecting element 1 is adjusted. Furthermore, because outer surface 21 of core body 8 is keyed and mates with keyways formed in inner portions 23, 24 of bores 22 of outer parts 16, 17, the outer parts 16,17 do not rotate when spindles 19, 20 are operated. Thus, rotationally fixed and torsion-resistant telescoping action of connecting element 1 is achieved. Spindles 19, 20 may be rotated by means known in the art, such as by engaging rims 32 of spindles 19, 20 with tools that extend through central holes 30a, 38a in end caps 30, 38, respectively. Advantageously, drive spindles 19, 20 can be operated from outside the ends of the connecting element 1, and permit a monolateral or bilateral extension of connecting element 1 without any mutual interaction between drive spindles 19, 20. Thus, outer parts 16, 17 provided at opposite ends of core body 8 can be moved about core body 8 independent of each other.

Dynamic adjustment of a bone fracture may be accomplished by relaxing the axial clamping of threaded spindle 20. Preferably, end cap 38 is threadably associated with connecting element 1, and by progressively unscrewing end cap 38 at distal end 52 of bore 22 in outer part 17, the rim 32 of spindle 20 is permitted to move. An elastic collar 40 is disposed between end cap 38 and outer part 17. Movement of rim 32 is constrained by end 34a of end cap 38, and as end cap 38 is unscrewed, rim 32 moves toward distal end 52 of bore 22 in outer part 17. A gap 40a is disposed proximate rim 32, permitting rim 32 to move toward distal end 52 of outer part 17 when end cap 38 is unscrewed. Elastic collar 40 holds end cap 38 in a selectable position, permitting dynamic adjustment and restricting release of end cap 38 from outer part 17. Thus, the axial displacement of outer part 17 may be achieved by a controllable amount, and preferably permits millimeter-by-millimeter incremental relaxation of the axial clamping of spindle 20.

Turning now to FIG. 3, an additional intermediate element 35 may be provided on the core body 8 between the extended outer parts 16, 17. Intermediate element 35 is axially movable on core body 8 and is also prevented from any rotational movement by means of a bore 37 having a cross section that matches the keyed shaft configuration of the core body 8. On one side of intermediate element 7, and preferably parallel to center axis 7, intermediate element 35 is split by a full-length, continuous slot 39. Intermediate element 35 may be positioned as desired along the free portion of core body 8 between outer parts 16, 17, and may be locked in its axial position by a clamping force applied by a fastening jaw 2. In particular, lower portion 54 of jaw 2 may be used to compresses or otherwise decrease the separation of upper and lower edges 39a, 39b of slot 39, thereby clamping intermediate element 35 in a fixed position on core body 8. In an alternate embodiment, intermediate element 35 may be provided with two continuous slots 39 on opposite sides of core body 8. Preferably, both slots 39 are disposed parallel to center axis 7. Advantageously, intermediate element 35 may have the same outer diameter as outer parts 16, 17.

Advantageously, connecting element 1 is internally extensible at both ends and, with the exception of the central region that forms when outer parts 16, 17 are separated from each other, connecting element 1 has a uniform outer diameter over its entire length. This facilitates the mounting of fastening jaws, and concomitantly the holding and fastening of bone screws, along the length of the connecting element. The provision of an intermediate element 35 permits the placement of one or more additional fastening jaws at a point between the outer parts in the region that otherwise has a smaller outer diameter than provided by outer parts 16, 17.

In addition, suitable selection of the material for core body 8, spindles 19, 20, and outer parts 16, 17 permits the degree of rigidity of connecting element 1 as a whole to be selectable. Suitable materials for the center part or core body 8, the drive mechanism such as spindles 19, 20 with threaded lead-screw-type shafts, and outer parts 16, 17 include aluminum, steel, carbon fibers, and titanium. Thus, by assembling connecting element 1 with a combination of components formed of different materials, the degree of rigidity of connecting element 1 may be controlled.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. For example, in an alternate embodiment, core body 8 may be the component having keyways, while outer parts 16, 17 have matching, keyed inner surfaces. In addition, geometries of keys and matching keyways other than those described herein and shown in the figures may be provided. Furthermore, only one drive spindle may be provided in some embodiments, and configurations other than lead-type screws may be used for separating the two outer parts. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An external bone fixation device comprising:
   a first support having outer and inner surfaces;
   a pair of second supports each having an inner surface slidably associated with the outer surface of the first support; and
   a driving mechanism disposed at least partially in contact with the inner surface of the first support and contained within at least one of the second supports,
   wherein the first support, second supports, and driving mechanism are coaxially disposed about a center axis, the outer surface of the first support is keyed to mate with the inner surfaces of the second supports to prevent rotation therebetween, and engagement of the driving mechanism with the first support permits the device to change overall length without rotation of the first and second supports with respect to each other.

2. The device of claim 1, wherein the first support has proximal and distal ends, the driving mechanism being engagable with at least one of the ends.

3. The device of claim 2, wherein the driving mechanism comprises at least one shaft threadably associated with the inner surface of the first support.

4. The device of claim 2, wherein the driving mechanism comprises a shaft threadably associated with the inner surface of the first support, and the axial positions along the center axis of the shaft and one of the second supports are fixed with respect to each other.

5. The device of claim 2, wherein the driving mechanism comprises a shaft threadably associated with the inner surface of the first support, and the axial positions along the center axis of the shaft and one of the second supports are movable with respect to each other.

6. The device of claim 2, wherein the driving mechanism comprises two shafts threadably associated with the inner surface of the first support, with each shaft being dependently engageable with an end of the first support.

7. The device of claim 6, wherein the second supports have a uniform diameter over substantially their entire length.

8. The device of claim 2, wherein each second support has a proximal end and a distal end, and the device further comprises a pair of caps, with each cap abutting an end of the driving mechanism and the distal end of one of the second supports.

9. The device of claim 8, wherein at least one of the caps is movable along the center axis so that the driving mechanism is permitted to move axially along the central axis therewith.

10. The device of claim 2, further comprising a cap disposed proximate an end of the driving mechanism, wherein the cap has a through hole and the driving mechanism has a recess, with the through hole and recess disposed generally along the same axis for receiving a tool.

11. The device of claim 1, wherein the inner surfaces of the second supports comprise keyways that mate with the keyed outer surface of the first support to prevent rotation therebetween.

12. The device of claim 1, further comprising an intermediate support positioned between the second supports and disposed upon the first support about the central axis.

13. The device of claim 1, wherein the driving mechanism comprises a pair of spindles with each spindle contained within one of the second supports.

14. The device of claim 1, wherein the outer surface of the first support and the inner surfaces of the second supports each comprise a polygonal shape.

15. The device of claim 1, wherein the driving mechanism comprises a first spindle having a first length, and each second support has a proximal end and a distal end with a second length defined therebetween, wherein the first length is shorter than the second length and the first spindle is disposed between the ends of one of the second supports.

16. The device of claim 15, wherein the driving mechanism further comprises a second spindle disposed between the ends of the other of the second supports.

17. An external bone fixation device comprising a first support having outer and inner surfaces, a pair of second supports slidably engagable with the outer surface of the first support, and a driving mechanism disposed at least partially in contact with the inner surface of the first support, wherein the first support, second supports, and driving mechanism are coaxially disposed about a center axis and engagement of the driving mechanism with the first support permits the device to change overall length without rotation of the first and second supports with respect to each other;

further comprising an intermediate support positioned between the second supports and disposed upon the first support about the central axis;

wherein the intermediate support and the second supports have outer diameters that are substantially the same, and the intermediate support has a longitudinal slot to facilitate placement of the intermediate support on the first support.

18. A telescoping device for supporting external bone fixation clamps comprising:

a first member having outer and inner surfaces;

a pair of second members each having an inner surface slidably engagable with the outer surface of the first member; and a pair of spindles each disposed at least partially in contact with the inner surface of the first member and each contained within one of the second members, wherein the first member, second members, and spindles are coaxially disposed about a center axis, the outer surface of the first member is keyed to mate with the inner surfaces of the second members to prevent rotation therebetween, and engagement of at least one the spindles with the first member permits the device to change overall length without rotation of the first and second supports with respect to each other.

19. The telescoping device of claim 18, wherein the first member has proximal and distal ends, and each spindle threadably engages one of the ends.

20. A telescoping support for use in external bone fixation comprising:

a first sleeve;

a pair of second sleeves each having a proximal end and a distal end, with each second sleeve receiving a portion of the first sleeve and slidably associated therewith;

a pair of spindles each comprising a shaft portion and a rim;

a pair of end caps each disposed proximate one of the rims;

wherein each spindle is disposed between the proximal and distal ends of one of the second sleeves, each spindle is operatively associated with the first sleeve, and the first sleeve and second sleeves are configured and dimensioned to prevent rotation with respect to each other.

* * * * *

UNITED STATES PATENT AND TRADEMARK OFFICE
CERTIFICATE OF CORRECTION

PATENT NO.    : 6,500,177 B1
DATED         : December 31, 2002
INVENTOR(S)   : Martinelli et al.

It is certified that error appears in the above-identified patent and that said Letters Patent is hereby corrected as shown below:

<u>Column 7,</u>
Lines 13-14, replace "dependently" with -- independently --.

Signed and Sealed this

Twenty-ninth Day of April, 2003

JAMES E. ROGAN
*Director of the United States Patent and Trademark Office*